(12) United States Patent
Hahn

(10) Patent No.: US 7,041,275 B2
(45) Date of Patent: May 9, 2006

(54) IRRIGATING FLUID

(75) Inventor: Robert Hahn, Eklidsvägen 12, SE-146 40, Tullinge (SE)

(73) Assignee: Robert Hahn, Tullinge (SE)

( * ) Notice: Subject to any disclaimer, the term of this patent is extended or adjusted under 35 U.S.C. 154(b) by 266 days.

(21) Appl. No.: 10/472,943

(22) PCT Filed: Mar. 15, 2002

(86) PCT No.: PCT/SE02/00467

§ 371 (c)(1),
(2), (4) Date: Nov. 6, 2003

(87) PCT Pub. No.: WO02/078688

PCT Pub. Date: Oct. 10, 2002

(65) Prior Publication Data

US 2005/0074412 A1    Apr. 7, 2005

(30) Foreign Application Priority Data

Mar. 30, 2001 (SE) .................................... 0101128

(51) Int. Cl.
*A61K 49/00* (2006.01)
*A61K 33/00* (2006.01)
*A61B 5/08* (2006.01)

(52) U.S. Cl. ........................ 424/9.1; 424/9.2; 424/10.4; 424/9.52; 424/718; 600/529; 600/532

(58) Field of Classification Search ................. 424/9.1, 424/9.2, 9.52, 10.4, 718; 600/529, 532
See application file for complete search history.

(56) References Cited

U.S. PATENT DOCUMENTS 6,180,059 B1 * 1/2001 Divino et al. .................. 422/45

FOREIGN PATENT DOCUMENTS

| GB | 2 234 897 | 2/1991 |
| WO | WO 97/17989 | 5/1997 |

OTHER PUBLICATIONS

Robert G. Hahn et al., "*Patterns of Irrigating Fluid Absorption During Transurethral Resection of the Prostate as Indicated by Ethanol*", The Journal of Urology, Mar. 1993, pp. 502 to 506, vol. 149.
R.G. Hahn, "*Irrigating Fluids in Endoscopic Surgery*", British Journal of Urology, 1997, pp. 669 to 680, vol. 79.
Robert G. Hahn, *The Use of Ethanol to Monitor Fluid Absorption During Transurethral Resection of the Prostate*, Scand J. Urol. Nephrol., 1999, pp. 277 to 283, vol. 33.
Robert G. Hahn, "*Transurethral Resection Syndrome From Extravascular Absorption of Irrigating Fluid*", Scand. J. Urol. Nephrol., 1993, pp. 387 to 394, vol. 27.
Joel Olsson et al., "*Survival After High-Dose Intravenous Infusion of Irrigating Fluids in the Mouse*", Urology, 1996, pp. 689 to 692, vol. 47.
R.G. Hahn, et al., "*Glycine 1.0% Versus Glycine 1.5% as Irrigating Fluid During Transurethral Resection of the Prostate*", British Journal of Urology, 1997, pp. 394-400, vol. 79.
Robert G. Hahn et al., "*Double-Blind Randomized Study of Symptoms Associated With Absorption of Glycine 1.5% or Mannitol 3% During Transurethral Resection of the Prostate*", The Journal of Urology, 1998, pp. 397 to 401, vol. 160.
Robert G. Hahn, "*Morphological and X-Ray Microanalytical Changes in Mammalian Tissue After Overhydration With Irrigating Fluids*", European Urology, 1996, pp. 355 to 361, vol. 29.
Robert G. Hahn, "*Transurethral Resection Syndrome After Transurethral Resection of Bladder Tumours*", Can. J. Anaesth., 1995, pp. 69 to 72, vol. 42.
Lars Sandfeldt et al., "*High-Dose Intravenous Infusion of Irrigating Fluids Containing Glycine and Mannitol in the Pig*", Journal of Surgical Research, vol. 95, 2001, pp. 114 to 125.

* cited by examiner

*Primary Examiner*—Sreeni Padmanabhan
*Assistant Examiner*—Ernst Arnold
(74) *Attorney, Agent, or Firm*—Buchanan Ingersoll PC

(57) ABSTRACT

A surgical irrigating fluid composition, especially for endoscopic surgery, is provided comprising a rinsing fluid and nitrous oxide added as a marker to the rinsing fluid in an amount which is detectable in the expired breath from a mammal, especially man, that is subjected to the surgery.

20 Claims, 5 Drawing Sheets

IRRIGATING FLUID

This application is a 371 of PCT/SE02/00467 filed on Mar. 15, 2002.

TECHNICAL FIELD

The present invention is within the field of irrigating fluids used in surgery on a mammal body, more specifically irrigating fluids containing a marker to enable detection of irrigating fluid absorbed by said body during surgery. The invention is based on the use of a new marker in such irrigating fluids, said new marker enabling a simple and proper monitoring of the irrigating fluid absorbed by the body while at the same time improving the conditions for the surgeon.

BACKGROUND OF THE INVENTION

Especially in endoscopic operations in the genitourinary tract the use of an irrigating fluid is required to gently dilate mucosal spaces and to remove blood and cut tissue from the operating field. There are several different irrigating fluids available commercially and the choice tends to be governed largely by tradition, although the price and properties of the fluid (e.g. stickiness and transparency) also play a role. The pharmacological effects of the fluid become important whenever it is absorbed by the patient. However, adverse reactions to irrigating fluids have not been documented as they have for drugs.

Most irrigating fluids were developed when the documentation of safety was much less important that it is today. Pharmacologists and regulatory authorities also pay little attention to solutions because they are conceived as devices (like soap and detergents) rather than drugs. Nevertheless, numerous reports of symptomatic and even fatal fluid absorption during TURP (transurethral resection of the prostate) and transcervical resection of the endometrium (TCRE, an operation for alleviating menorrhagia) emphasize the importance of using an irrigating fluid with a favourable profile of adverse effects.

For many years, little comparative data were available showing whether one irrigating fluid is more prone to adverse effects than others. However, during the past decade several studies covering this topic have been reported.

A summary of said reports and further details concerning irrigating fluids can be found in British Journal of Urology (1997), 79, 669–680. Some of said details will, however, be presented below.

Sterile water was used as irrigating fluid during the early years of TURP. However, obscure reactions with post-operative haemoglobulinuria sometimes occured and severe cases even led to death. Enrichment of the blood with salicylate and glucose when added to the sterile water made urologists realize, in 1947, that the absorption of the irrigating fluid into the circulation through severed prostatic veins must be the cause of the haemolysis. As electrolytes do not allow cutting by electrocautery, one or several non-electrolyte solutes capable of preventing haemolysis were then added to the irrigating fluid.

Glycine was the first suggested as suitable, and the other irrigating fluids used today, mannitol and mixtures of sorbitol and mannitol, were introduced somewhat later. An example of a document disclosing an irrigating fluid containing glycerine or mannitol is Journal of Surgical Research, Vol 95, 2001, pp 114–125. Reference can also be made to GB 2234897 A, which discloses the use of glycerine and L-arginine in an irrigating fluid.

Despite their non-haemolytic properties, absorption of the new irrigating fluids continued to be associated with adverse events which were often summarized as transurethral resection reactions (TUR syndrome). The clinical descriptions of this syndrome from the mid-1950s are still the cornerstones of our view of the risks associated with the use of irrigating fluids.

The uptake of small amounts of irrigating fluid occurs during almost every TURP and TCRE. The absorbed volume varies greatly and cannot be predicted in the individual patient, although it tends to be larger in extended and bloody operations. The uptake of 1 L of fluid, which corresponds to an acute decrease in the serum sodium concentration of 5–8 mmol/L, is the volume above which the risk of absorption-related symptoms is statistically increased.

Thus, in many cases the uptake of irrigating fluid, vascularly and extravascularly, is considerable. If said uptake exceeds 2–3 L the situation for the patient becomes lethal, and in more than 25% of actual cases the absorption has been reported to exceed 0.3 L.

Therefore, in addition to attempts to find an irrigating fluid composition which is absorbed to an extent as minor as possible, efforts have been made to find markers for such irrigating fluids by means of which absorbed amounts of fluid can be detected as early as possible.

One type of marker, or rather monitoring means, which is on the market, is a methodology where the patient is on a balance and his weight is checked. Such a methodology is, however, associated with considerable problems in calculating the amount fed to and removed from the patient during the course studied.

A different methodology is the use of ethanol as a marker added to the rinsing fluid. More specifically, ethanol is added to the fluid and the ethanol content of the air exhaled by the patient is recorded. The use of this new technique is disclosed in a number of documents, e.g. The Journal of Urology, Vol. 149, 502–506, March 1993, and U.S. Pat. No. 5,603,332. This method solved part of the problems but new problems arose instead. Thus, for instance, the speed of detection of exhaled ethanol is slow, the accuracy of detection of small amounts of ethanol is low and side effects with respect to the patient occur, such as dizziness and even alcohol dependence.

Primarily as a consequence of the non-accuracy of the method referred to a solute, especially glycine, has been added to the rinsing fluid (generally sterile water) so as to enhance the viscosity thereof, to reduce the absorbed amount of fluid, as well as to prevent or inhibit the heamolytic action thereof. However, by such a measure the irrigating fluid becomes less clear and the visibility for the surgeon is-reduced, which is a considerable disadvantage as a clear and good sight for the surgeon is an essential prerequisite for surgery of the kind referred to.

DISCLOSURE OF THE INVENTION

The present invention is based on the use of a new marker for irrigating fluids of the types referred to above. More specifically, it has been found that the gas nitrous oxide ($N_2O$) can be used as such a marker. Thus, the distribution kinetics of nitrous oxide makes it possible to measure the amount thereof in the expired breath from the patient during surgery of the kind disclosed above. Furthermore, said amount is essentially proportional to the absorbed amount of irrigating fluid. In addition thereto, the use of nitrous oxide in this respect shows great advantages as compared to the use of ethanol for the same purpose. Some of these advantages are the following.

When nitrous oxide is added as a marker, already small amounts of absorbed rinsing or irrigating fluid can be detected within seconds. In other words, the present invention enables the use of a very rapid and accurate detection of fluid absorbed by the animal body. Hence, necessary measures can be taken at an early stage and in fact before symptoms occur. In addition thereto, this generally means that pure rinsing fluid, such as sterile water, without any added solutes, can be used as the irrigating fluid, which eliminates the previous disadvantages connected with such additions. Furthermore, nitrous oxide can be added to the fluid in advance and kept in solution for several years if using a suitable container material. In addition thereto, the detection of exhaled nitrous oxide is very accurate and can be made with simple and even existing nitrous oxide monitors. For instance, such monitors are available in anesthesia machines, which monitors may be used as such or easily converted into more accurate monitors. In this context, it should even be possible to design a common monitor for the purpose of the present invention as well as for anesthesia. Finally, as concerns the known analgesic effect with i.v. nitrous oxide, such an effect should be very limited and should not constitute any problem.

More specifically, according to a first aspect of the present invention, there is provided a surgical irrigating fluid composition comprising a rinsing fluid and a fluid absorption marker, the characteristic feature of said composition being that said marker comprises nitrous oxide and is present in an amount which is detectable via a mammal, including human, body which is the subject of said surgery.

Although, in general, the marker used in accordance with the present invention is detectable at any suitable site of the mammal body, the most convenient way of detecting the same is via the expired breath from the mammal in question. Accordingly, in a preferable embodiment of the composition, said nitrous oxide is preferably present therein in an amount that is detectable in said expired breath.

The rinsing fluid referred to is selected in accordance with knowledge known per se in this technical field. Thus, it preferably comprises or consists of sterile water.

Although one of the great advantages with the present invention is that pure water could be used as rinsing fluid, it is of course also within the scope of the invention to utilise a viscosity-enhancing and/or haemolysis-preventing solute as an additive if this is required or preferable for some specific reason. Thus, one embodiment of the composition claimed is a composition wherein the rinsing fluid comprises or contains a haemolysis-preventing solute. Such a solute is generally selected in accordance with general knowledge within this field. Examples of preferable solutes in this respect are glycine, mannitol and sorbitol or mixtures thereof.

If used, said solute is preferably utilised within the range of 0.1–5.0% by weight, more preferably 0.5–2.5% by weight, and even more preferably 1.0–2.0% by weight, based on the weight of said rinsing fluid.

In general, the nitrous oxide is present in the rinsing fluid in such an amount that the concentration of nitrous oxide in the expired breath from the mammal subjected to the surgery in question is detectable by any nitrous oxide monitor. However, preferably the amount or concentration thereof in the rinsing fluid is 0.1–3.0% by weight, more preferably 0.5–2.5% by weight, and most preferably 0.7–1.5% by weight, based on the weight of said rinsing fluid. Generally, however, said concentration may be up to the saturation level of the nitrous oxide in said rinsing fluid at normal pressure and room temperature, such as eg. 0.01–0.65 L of nitrous oxide per L of rinsing fluid. Useful ranges within said broad range are 0.01–0.5, or 0.05–3, L/L.

The nitrous oxide gas is preferably dissolved in the rinsing fluid and stored together with said rinsing fluid up to the use of said fluid in surgery. However, it is of course also within the scope of protection to add the gas separately in connection with the surgery to be performed, as in general similar effects should be obtainable by any of these methods.

According to another aspect of the invention, or expressed in another way, there is also provided a composition for use as an irrigating fluid for surgery in a mammal, including man, said composition being defined in the same way as the composition and its embodiments described above.

Still another aspect of the invention is represented by a composition as defined above, for use as a monitoring fluid in a diagnostic method for the determination of the amount of irrigating fluid which is absorbed by a mammal, including man, during a surgery. Also in this respect the embodiments described above are applicable.

The invention could also be defined as the use of nitrous oxide for the determination of the amount of irrigating fluid which is absorbed during surgery in a mammal, including man.

Since, as was mentioned above, the detection of nitrous oxide in the expired breath from a mammal could be made by a nitrous oxide monitoring device known per se, a single general inventive concept of the present invention is also represented by the use of a nitrous oxide detector as a device for monitoring the amount of irrigating fluid composition which is absorbed by a mammal, including man, in surgery, said irrigating fluid composition being as defined above.

A final aspect of the invention is represented by a method of monitoring the amount of irrigating fluid composition which is absorbed by a mammal, including man, in surgery, the irrigating fluid composition being as defined above, which method is characterized by monitoring the expired breath from said mammal by means of a nitrous oxide detector to detect the amount of nitrous oxide therein.

Thus, in connection with the last two aspects of the present invention, the nitrous oxide monitoring device, or detector, could be selected among previously known nitrous oxide detectors used in other connections, or easily modified therefrom.

Generally, the surgery referred to in connection with the different aspects of the invention is endoscopic surgery, preferably endoscopic surgery in the genitourinary tract. In this context an especially preferable embodiment of the invention is represented by the case where said endoscopic surgery in the genitourinary tract is transurethral resection (TURP) or transcervical resection of the endometrium (TRCE).

The present invention is exemplified by the following non-limiting working example.

EXAMPLE

A number of tests on pigs were performed according to the protocols and with the results presented below.

Addition of Nitrous Oxide to the Irrigating Fluid

The irrigating fluid (Baxter) contained 30 mg of mannitol and 1 mg of ethanol per mL. To a bag with 3 L fluid 300 mL of nitrous oxide (=0,18 mg nitrous oxide/mL irrigagting fluid) were added. The nitrous oxide was measured with a 300 mL glass syringe and injected into the bag using the syringe connection. The temperature was abut 22° C. and the air pressure about 1015 mbar (not measured but estimated via meteorological service). Before the addition of nitrous oxide the gas in the bag was removed, about 1 mL remained. After the addition of nitrous oxide the bag was shaken until the nitrous oxide was dissolved. A gas bubble with a volume of abut 15 mL remained. A rough calculation indicated that the bubble consisted of 20% nitrous oxide and 80% air gases.

Measurement of Nitrous Oxide in Exhaled Air

A Telair N2O monitor type 2001 L was used to measure the nitrous oxide concentration. The measuring range of the instrument was 0–1000 ppm.

As the analyser was sensitive also to carbon dioxide an absorber containing soda lime to remove the carbon dioxide was arranged before the analyser. During the absorption process water is formed which together with the moisture in the exhaled air can disturb the measurements. A layer of silica gel after the soda lime absorber was used to eliminate this problem.

The sample gas pump gave a sample flow of 300 mL/min. Due to the volume of the absorber the instrument had a response time of about 10 seconds.

The pump was continuously pumping gas. The measured concentration was a time weighted average for the exhaled and inhaled gas.

Description of Tests

Pig. 1.

The weight of the pig was 19 kg. Ventilation 3L/min with 20 breaths per minute, 25% inhalation followed by 10% pause. At the first test 300 mL of irrigating fluid were injected intravenously during 20 min using a dosing pump. A second test with intraperitonal injection of 600 mL irrigating fluid failed because of problems with the analyser, probably caused by condensation of water in the sensor.

Pig 2.

The weight of the pig was 21 kg. Ventilation as for pig. 1. First 300 mL of irrigating fluid were injected intraperitonally during 20 minutes. The initial decrease in nitrous oxide concentration was caused by placing the needle in the wrong place. Some mL were injected before the injection was stopped and the test restarted. The decrease is the decay phase from the first injection.

In test two 600 mL were administered intravenously during 20 minutes.

Pig 3

Weight 23 kg. Ventilation 3,5 mL/min, the rest as for pig 1. First a number of tests with intravenous injection of pulses of fluid were performed. The volumes added were 2, 10 and 20 mL. Approximately 1 mL/s was added.

Then 150 mL of fluid were administered intravenously during 20 minutes. The discontinuity in the diagram was caused by testing another ventilator setting which affected the reading so much that the data point was not used. After 40 minutes 600 mL of irrigating fluid were added intravenously during 20 minutes.

Results

The results are presented in the accompanying drawings, in which

Figure 1:
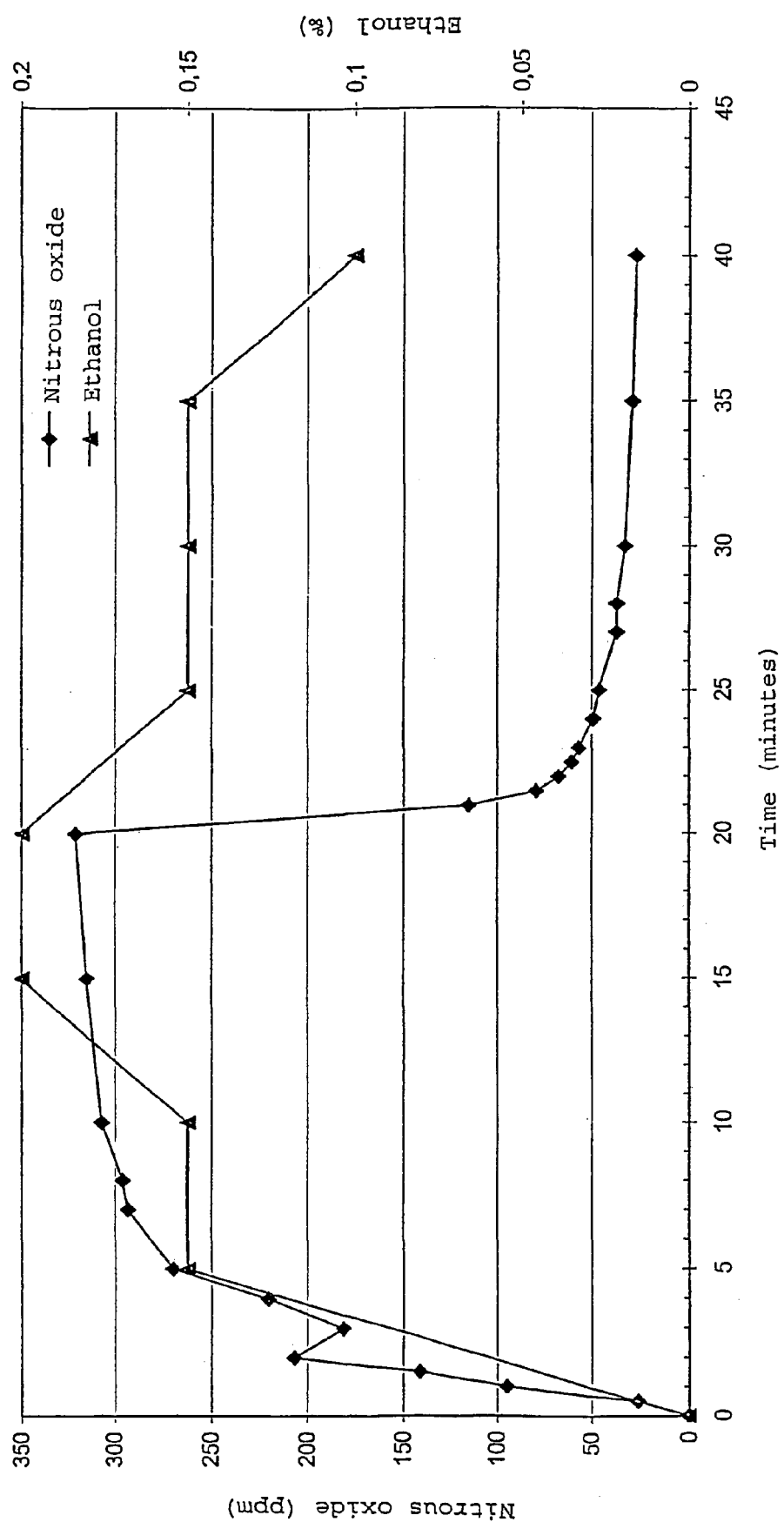
FIG. 1 shows a graph for pig 1 concerning concentration of nitrous oxide and of ethanol versus time in exhaled air from pig 1 with intravenous administration.
Figure 2:
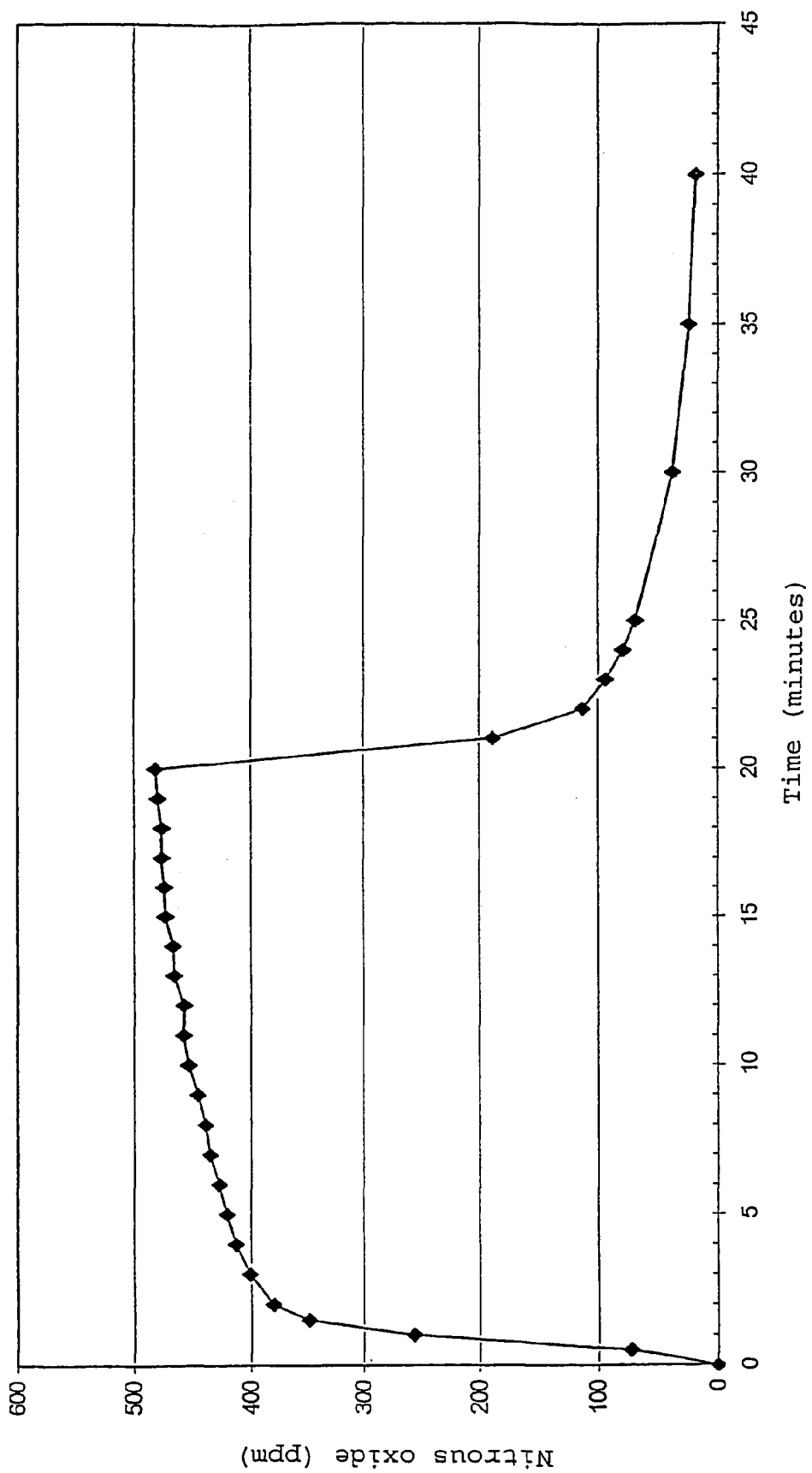
FIG. 2 shows a graph for pig 2 concerning concentration of nitrous oxide versus time in exhaled air with intravenous administration.
Figure 3:
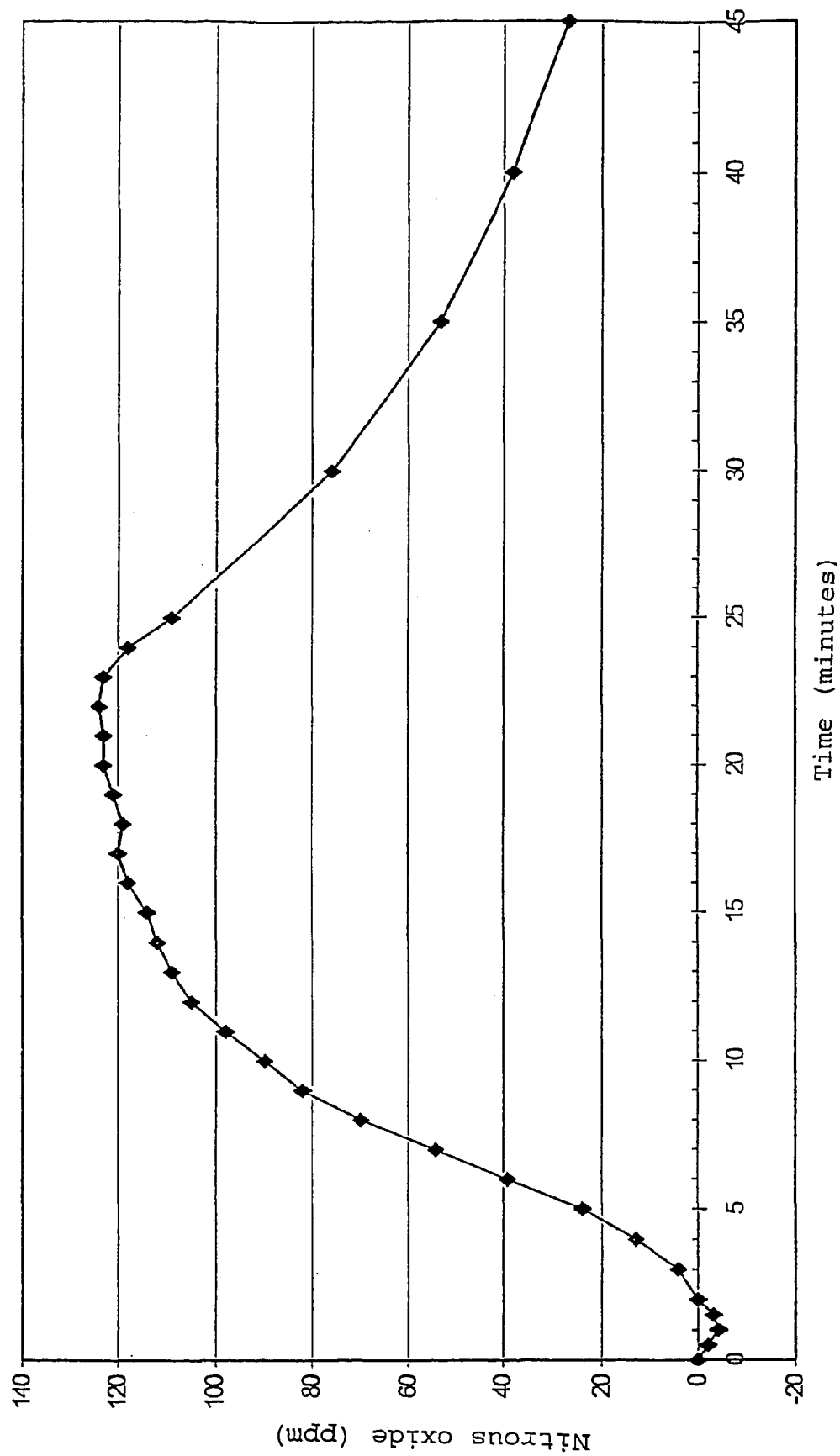
FIG. 3 shows a graph for pig 2 concerning concentration of nitrous oxide versus time in exhaled air with intraperifoneal administration.
Figure 4:
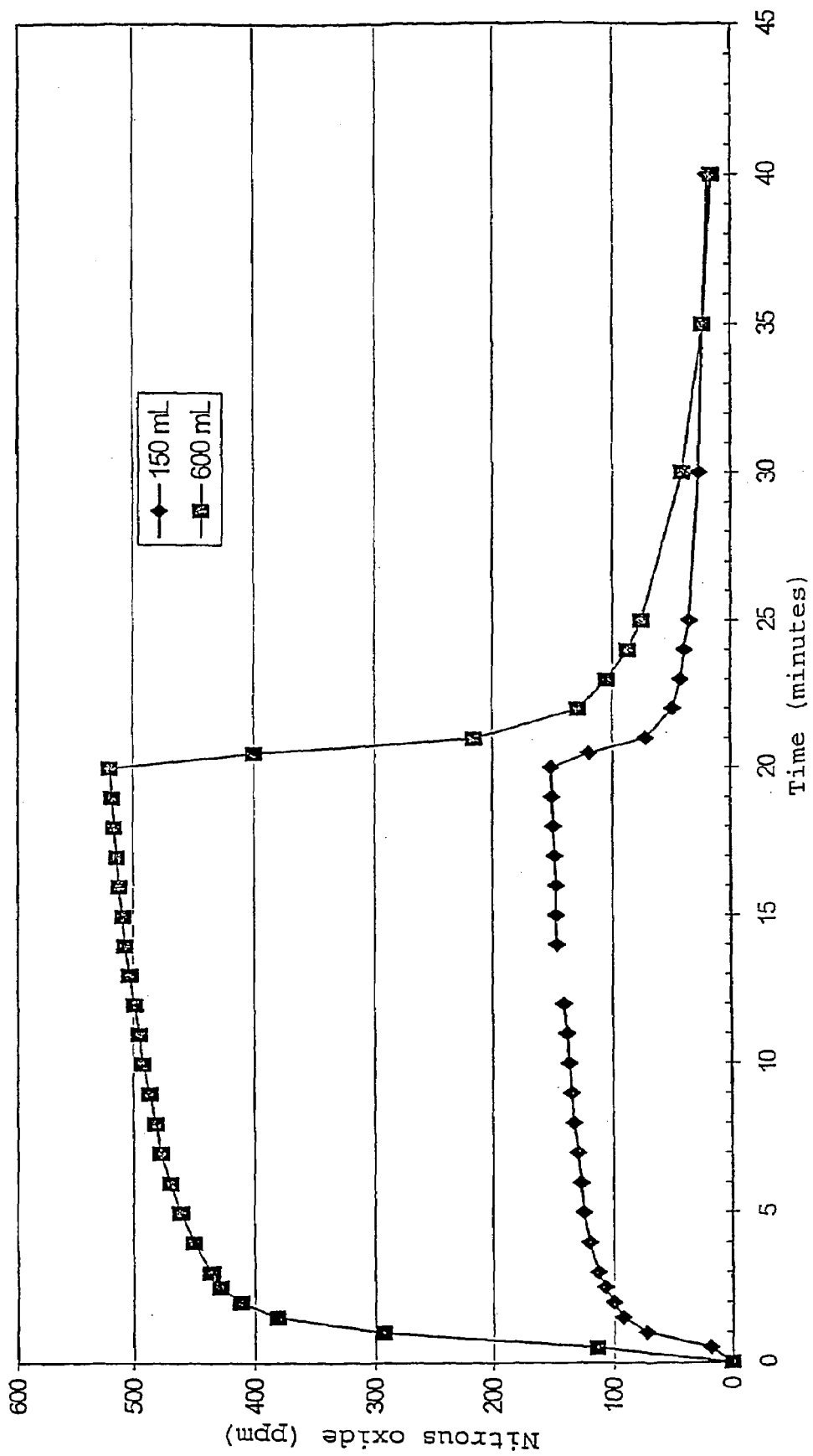
Figure 5:
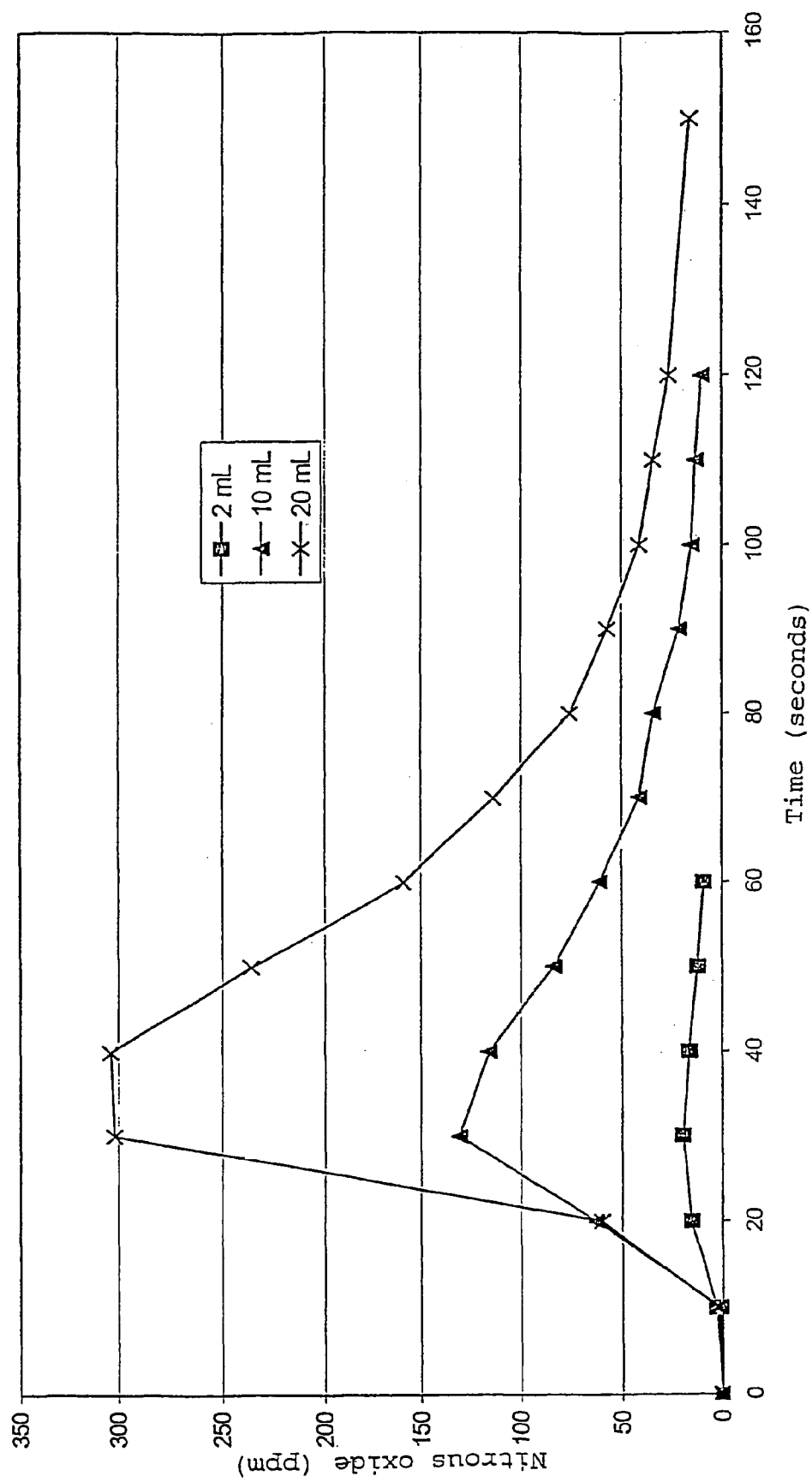

FIG. 4 shows a graph for pig 3 concerning concentration of nitrous oxide versus time in exhaled air with intravenous administration, and FIG. 5 shows a graph for pig 3 concerning concentration of nitrous oxide versus time in exhaled air from pig 2 with intravenous injection of pulses of irrigating fluid.

The nitrous oxde concentration values are measured concentrations minus the starting point value. In some cases a test was started while the nitrous oxide concentration from the previous test was still decreasing. As the base line was not stable, the values at the end of the decay phase are uncertain. This can be seen in FIG. 4, where it looks like the 150 mL concentration values are stabilizing at a higher level than the 600 mL values.

The instrument used for measuring the ethanol concentration showed the concentration in steps of 0.05% and the highest measured concentration was 0.20%. The resolution was not good enough for an uncorrected cmparison with nitrous oxide. However, when normalising the data to similar peak heights it was possible to see that the nitrous oxide concentration decreased much faster than the ethanol.

When injecting irrigating fluid intravenously, the nitrous oxide concentration started to increase about 15 seconds after start of injection. 50% of the final concentration-was reached about one minute before the nitrous oxide concentration started to increase. 50% of the final concentration was reached about one minute after the concentration started to increase. At intraperitoneal injection it took 2.5 minutes before the nitrous oxide concentration started to increase. 50% of the final concentration was reached about 5 minutes after the start of the increase.

When pulsed fluid were added intravenously the nitrous oxide concentration increased 10–15 ppm per mL of irrigating fluid. The instrument showed the peak reading about 30 seconds after start injection.

The tests show that the nitrous oxide concentration can be measured continuously with high sensitivity.

A nitrous oxide mass balance was made for pig 3. The irrigating fluid contained 0.1 mL/mL and 30 mL/min were added.

Added amount of nitrous oxide: 30 mL/min×0,1 mL=3,0 mL/min.

Exhaled nitrous oxide: (3,5+0,3)L/min×520 ppm×0,001 (mL/L)/ppm×100/65=3,0 mL/min.

The factor 100/65 was used due to the fact that inhalation was 25% of the breathing cycle followed by 10% pause. The analyser therefore sampled an average concentration which was 65% of the concentration in the exhaled gas. The sample gas flow was assumed to be 0.3 L/min this flow should be added to the ventilation flow from the pig.

The invention claimed is:

1. A method of monitoring the amount of irrigating fluid composition which is absorbed during surgery in a mammal, including man, comprising utilizing an irrigating fluid composition comprising nitrous oxide as a marker in a detectable amount, and monitoring the expired breath from said mammal by means of a nitrous oxide detector to detect the amount of nitrous oxide therein.

2. A method according to claim 1 wherein said surgery is endoscopic surgery.

3. A method according to claim 2 wherein said endoscopic surgery is conducted in the genitourinary tract.

4. A method according to claim 3, wherein endoscopic surgery in the genitourinary tract is a transurethral resection or transcervical resection of the endometrium.

5. A method according to claim 1 wherein said irrigating fluid composition comprises sterile water and nitrous oxide as a marker.

6. A method according to claim 1 wherein said irrigating fluid composition contains a solute for inhibiting hemolysis.

7. A method according to claim 6 wherein said solute is selected from the group consisting of glycine, mannitol, and sorbitol, and mixtures thereof.

8. A method according to claim 6 wherein said solute is within the range of 0.1–5.0% by weight based on the weight of said irrigating fluid composition.

9. A method according to claim 7 wherein said solute is within the range of 0.1–5.0% by weight based on the weight of said irrigating fluid composition.

10. A method according to claim 6 wherein said solute is within the range of 0.5–2.5% by weight based on the weight of said irrigating fluid composition.

11. A method according to claim 7 wherein said solute is within the range of 0.5–2.5% by weight based on the weight of said irrigating fluid composition.

12. A method according to claim 6 wherein said solute is within the range of 1.0–2.0% by weight based on the weight of said irrigating fluid composition.

13. A method according to claim 7 wherein said solute is within the range of 1.0–2.0% by weight based on the weight of said irrigating fluid composition.

14. A method according to claim 1 wherein the amount of nitrous oxide in the irrigating fluid composition is within the range of 0.1–3.0% by weight based on the weight of said irrigating fluid composition.

15. A method according to claim 6 wherein the amount of nitrous oxide in the irrigating fluid composition is within the range of 0.1–3.0% by weight based on the weight of said irrigating fluid composition.

16. A method according to claim 1 wherein the amount of nitrous oxide in the irrigating fluid composition is within the range of 0.5–2.5% by weight based on the weight of said irrigating fluid composition.

17. A method according to claim 6 wherein the amount of nitrous oxide in the irrigating fluid composition is within the range of 0.5–2.5% by weight based on the weight of said irrigating fluid composition.

18. A method according to claim 1 wherein the amount of nitrous oxide in the irrigating fluid composition is within the range of 0.7–1.5% by weight based on the weight of said irrigating fluid composition.

19. A method according to claim 6 wherein the amount of nitrous oxide in the irrigating fluid composition is within the range of 0.7–1.5% by weight based on the weight of said irrigating fluid composition.

20. A method according to claim 1 wherein said mammal is a human.

* * * * *